United States Patent [19]
Brucato et al.

[11] Patent Number: 6,100,072
[45] Date of Patent: Aug. 8, 2000

[54] RECOMBINANT RABBIT TISSUE FACTOR BASED PROTHROMBIN TIME REAGENT

[75] Inventors: Cheryl Brucato, Andover; Cynthia Birr; Pau Bruguera, both of Lexington; Juan Ruiz, Acton; Demetrio Sanchez-Martinez, Lynnfield, all of Mass.

[73] Assignee: Instrumentation Laboratory S.p.A., Milan, Italy

[21] Appl. No.: 09/064,378

[22] Filed: Apr. 22, 1998

Related U.S. Application Data

[60] Provisional application No. 60/044,541, Apr. 23, 1997.

[51] Int. Cl.[7] .......................... C12P 21/04; A61K 35/14; C07K 1/00
[52] U.S. Cl. .......................... 435/69.7; 435/69.6; 435/6; 530/381; 530/415; 530/830
[58] Field of Search ................................. 435/69.6, 69.7; 530/381, 415, 830

[56] References Cited

U.S. PATENT DOCUMENTS

| | | | |
|---|---|---|---|
| 4,755,461 | 7/1988 | Lawson et al. | 435/13 |
| 5,223,427 | 6/1993 | Edgington et al. | 435/240 |
| 5,254,350 | 10/1993 | Barrow et al. | 424/570 |
| 5,270,451 | 12/1993 | Hawkins et al. | 530/381 |
| 5,314,695 | 5/1994 | Brown | 424/450 |
| 5,358,853 | 10/1994 | Butler et al. | 435/13 |
| 5,374,617 | 12/1994 | Morrissey et al. | 514/8 |
| 5,391,380 | 2/1995 | Barrow et al. | 424/570 |
| 5,418,141 | 5/1995 | Zweig et al. | 435/13 |
| 5,426,031 | 6/1995 | Hawkins et al. | 435/13 |
| 5,472,850 | 12/1995 | Morrissey | 435/13 |
| 5,502,651 | 3/1996 | Jackson et al. | 364/509 |
| 5,504,064 | 4/1996 | Morrissey et al. | 514/8 |
| 5,504,067 | 4/1996 | Morrissey et al. | 514/8 |
| 5,508,170 | 4/1996 | Butler et al. | 435/13 |

FOREIGN PATENT DOCUMENTS

| | | |
|---|---|---|
| 88/07543 | 10/1988 | WIPO . |
| 92/08479 | 5/1992 | WIPO . |
| 93/07492 | 4/1993 | WIPO . |
| 93/13211 | 7/1993 | WIPO . |
| 93/23074 | 11/1993 | WIPO . |

OTHER PUBLICATIONS

Hochuli et al. (1988), "Genetic Approach to Facilitate Purification of Recombinant Proteins with a Novel Metal Chelate Absorbent", *Bio/Technology*, 6 (11): 1321–1325.

Hemker et al. (1996), "Proteins induced by vitamin K absence (PIVKAs): effect of coumarins on circulating clotting factors", in *Oral Anticoagulants*, Poller and Hirsch, eds., Arnold Press, London, pp. 65–75.

"Pel–Freez Molecular Diagnostics recombinant Rabbit Tissue Factor", *Pel–Freez Biologicals*, Jan. 1997, pp. 1–5.

Andrews et al. (1991), "Conservation of tissue factor primary sequence among three mammalian species", *Gene*, 98: 265–269.

Denson et al. (1995), "Validity of the INR System for Patients with Liver Impairment", *Thrombosis and Haemostasis*, 73 (1): 162.

Kovacs et al. (1994), "Assessment of the Validity of the INR System for Patients with Liver Impairment", *Thrombosis and Haemostasis*, 71 (6): 727–30.

Baele et al. (1996), "Comparison of a Recombinant Thromboplastin with Thrombotest for Oral Anticoagulant Control", *Haemostasis*, 26 (1): 11–15.

Kitchen et al. (1996, "Two Recombinant Tissue Factor Reagents Compared to Conventional Thromboplastins for Determination of International Normalised Ratio: A thirty–three–laboratory Collaborative Study", *Thrombosis and Haemostasis*, 76 (3): 372–376).

Roussi et al. (1994), "French Multicentric Evaluation of Recombinant Tissue Factor (Recombiplastin) for determination of Prothrombin Time", *Thrombosis and Haemostasis*, 72 (5): 698–704.

Forastiero et al. (1994), "Evaluation of Recently Described Tests for Detection of the Lupus Anticoagulant" *Thrombosis and Haemostasis*, 72 (5): 728–733.

Tripodi et al. (1992), "Recombinant Tissue Factor as Substitute for Conventional Thromboplastin in the Prothrombin Time Test", *Thrombosis and Haemostasis*, 67 (1): 42–45.

Bader et al. (1994), "Multicentric Evaluation of a New PT Reagent Based on Recombinant Human Tissue Factor and Synthetic Phospholipids", *Thrombosis and Haemostasis*, 71 (3): 292–299.

Kolde (1995), "Standardization of the Prothrombin Time: Clinical Results with a Recombinant Tissue Factor Reagent", *Haematologica*, 80 (supplement to No. 2): 7–13.

D'Angelo (1995), "Prothrombin Time Standardization: The Problem of the Control Plasma", *European Journal of Clinical Chemistry and Clinical Biochemistry*, 33 (12): 1019–1022.

*Primary Examiner*—Karen Cochrane Carlson
*Assistant Examiner*—Holly Schnizer
*Attorney, Agent, or Firm*—Testa, Hurwitz & Thibeault, LLP

[57] ABSTRACT

Liquid and lyophilized reagents for determining prothrombin time and/or fibrinogen levels in a plasma sample are disclosed. The reagents preferably are based on recombinant rabbit tissue factor. Also disclosed is a purified preparation of recombinant rabbit tissue factor having unique properties, and a novel method for making PT reagents.

19 Claims, 1 Drawing Sheet

RECOMBINANT RABBIT TISSUE FACTOR BASED PROTHROMBIN TIME REAGENT

RELATED APPLICATION

Priority is claimed to provisional application Ser. No. 60/044,541, filed Apr. 23, 1997.

FIELD OF THE INVENTION

The present invention relates generally to the field of prothrombin time reagents for determining deficiencies in the coagulation system; and more particularly to reagents for prothrombin time tests made using recombinant rabbit tissue factor, and phospholipids from either a natural or synthetic source. The present invention also includes a preparation of purified recombinant rabbit tissue factor, and novel methods for making the reagents.

BACKGROUND OF THE INVENTION

Tissue factor, also called thromboplastin, is a membrane-associated glycoprotein which functions by forming a complex with blood coagulation Factors VII and VIIa. The activity of tissue factor depends on the presence of phospholipids, which are associated with the protein. Bach, Ronald R., "Initiation of Coagulation by Tissue Factor", CRC *Critical Reviews in Biochemistry* 23(4):339–368 (1988). The complexing of Factors VII and VIIa with tissue factor greatly enhances their proteolytic activity. The complex activates a series of enzymes that comprise the extrinsic and common pathways of the coagulation cascades, ultimately leading to the formation of thrombin, which catalyzes the conversion of fibrinogen into fibrin, resulting in clot formation. Nemerson, Yale, "Tissue Factor and Hemostasis" *Blood* 71:1–8 (1988).

Diagnostic tests, such as the prothrombin time (PT) test, utilize this series of enzymatic events in vitro under controlled conditions to diagnose deficiencies in the blood coagulation systems of patients, and to monitor patients on anticoagulant therapy. In the PT test, a reagent which induces coagulation is added to a sample of the patient's plasma. All PT reagents contain tissue factor as a coagulation inducing ingredient. The time it takes for clot formation to occur in the plasma sample is the prothrombin time or PT value. Most commercially available PT reagents contain crude tissue factor extracted from natural sources, e.g., rabbit brain, rabbit brain/lung mixtures, human placenta or bovine brain. The crude extracts, because they are natural products, often lack lot to lot uniformity. For example, rabbit brain thromboplastins show seasonal variability. Another problem with natural extracts is the presence of contaminants. For example, human tissue factor may be a source of HIV or other human viral diseases and many natural-sourced thromboplastins also contain other extraneous coagulation factors which can detrimentally affect the PT value.

In an attempt to overcome some of these problems, recombinant tissue factors have been used to make PT reagents. For example, a prothrombin time reagent based on recombinant human tissue factor is described in published PCT Application WO93/07492. However, human tissue factor is sensitive to proteins induced by vitamin K absence or antagonists (PIVKAs), which has been shown to alter the PT time and give an inaccurate result in the PT test (Kovacs M. J. et al, "Assessment of the validity of the INR system for patients with liver impairment." *Thromb Haemost*, (1994); 71:727–30 and Spaethe, R. and Shirley, I. "Comparison of a highly sensitive rabbit brain thromboplastin, Dade Thromboplastin FS, with a human brain thromboplastin, Manchester Comparative Thromboplastin" in *Thromboplastin Calibration and Oral Anticoagulant Control*, A.M.H.P. van den Besselaar, H. R. Gralnick and S. M. Lewis, editors. Martinus Nijhoff Publishers, (1984), pp. 197–206). PIVKAs often are present in patients on anticoagulant therapy, or patients having a liver disease or other disorder which causes a vitamin K deficiency. Therefore, PT reagents based on human tissue factor may provide inaccurate PTs when used with plasma samples from patients with elevated PIVKA levels.

SUMMARY OF THE INVENTION

The invention relates to prothrombin time reagents containing recombinant rabbitderived tissue factor, a preparation of recombinant rabbit tissue factor and methods of making reagents based on recombinant tissue factors. The invention further relates to methods for determining PT values and fibrinogen levels in plasma samples using the reagents of the present invention.

In one aspect, the invention relates to a reagent for determining prothrombin time and/or fibrinogen levels in a plasma sample in which the reagent comprises recombinant tissue factor protein, a phospholipid selected from the group consisting of phosphatidylcholine, phosphatidylserine and combinations thereof, a buffer system and calcium ions. The reagent can be in liquid form or lyophilized, and optionally may contain other ingredients, including stabilizers, antimicrobial agents, biocides, etc.

In another aspect, the invention relates to a purified preparation of recombinant rabbit tissue factor having valuable properties. The present recombinant rabbit tissue factor comprises an amino acid sequence defining from an N-terminus to a C-terminus: an extracellular domain, a lipid binding domain, an intracellular domain, and an affinity tag for selectively enriching the recombinant tissue factor. The purified preparation is enriched for recombinant tissue factor protein having the lipid binding domain, relative to recombinant rabbit tissue factor protein lacking the affinity tag.

In another aspect, the invention relates to a relipidation method for preparing a reagent for determining PT or fibrinogen levels. The method comprises the steps of (a) providing a solution, suspension or dispersion containing phospholipid vesicles; (b) admixing tissue factor protein with the solution, suspension or dispersion; and (c) incubating the mixture under conditions and for a time sufficient to permit the protein to associate with the phospholipid vesicles. The method can be used with natural or recombinant tissue factor proteins. The protein preferably is a recombinant tissue factor protein. In a currently preferred embodiment, the protein is recombinant rabbit tissue factor protein; more particularly, the purified recombinant rabbit tissue factor preparation described herein. The invention further comprises reagents produced by the method.

DETAILED DESCRIPTION

Figure 1:
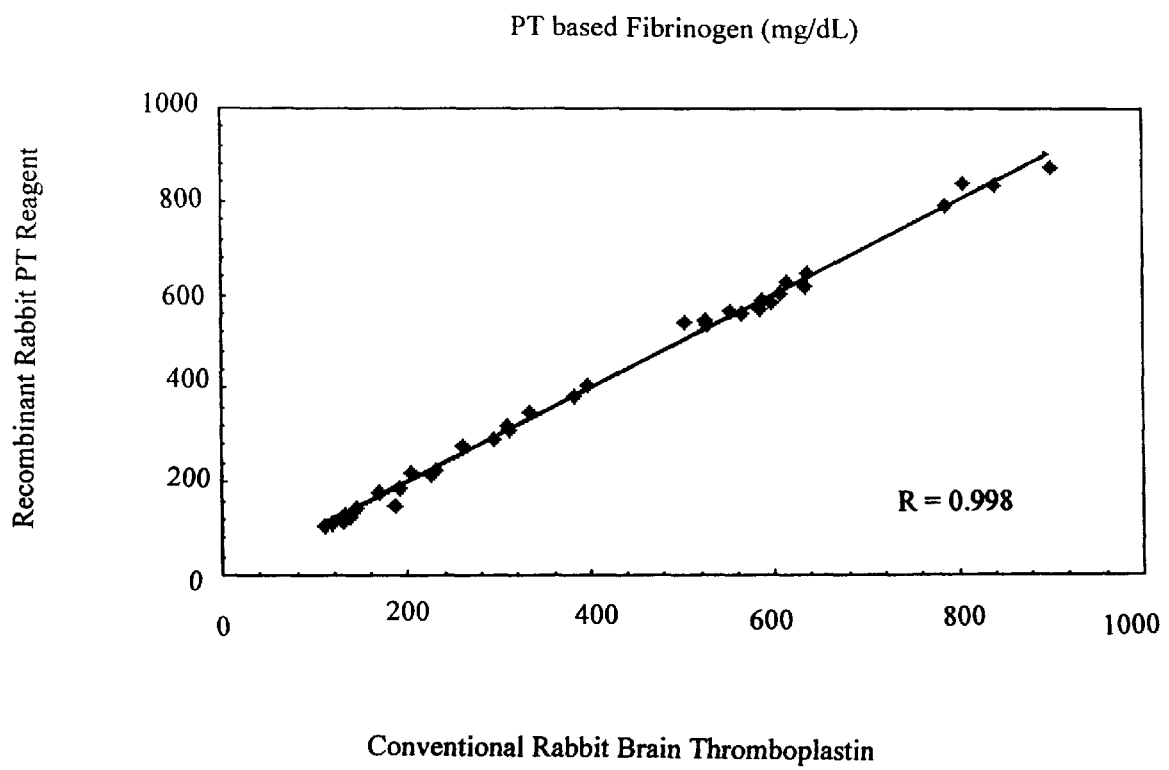
FIG. 1 is a graph showing a comparison of fibrinogen levels determined using a prothrombin time reagent based on conventional rabbit tissue factor versus a reagent based on recombinant rabbit tissue factor.

A reagent based on recombinant tissue factor with defined phospholipids and other stabilizers has been developed. This reagent may be either a liquid or lyophilized formulation, and is useful for determining fibrinogen levels, percent coagulation factor activity, prothrombin time, percent PT activity, PT ratio, and International Normalized Ratio (INR) in a patient sample using clinical coagulation instruments or by manual methods.

The reagent comprises, at a minimum, recombinant tissue factor protein ("tissue factor" is also sometimes referred to herein as "thromboplastin"), phospholipids selected from the group consisting of phosphatidylcholine, phosphatidylserine and combinations thereof, a buffer system and calcium ions. The reagent preferably further comprises other ingredients, including, for example, stabilizers, antimicrobial agents and/or biocides. In a currently preferred embodiment, the recombinant tissue factor protein is recombinant rabbit tissue factor protein, and the phospholipids are synthetic phospholipids. The ratio of tissue factor protein to lipid can be from about 0.05 µg protein per mg phospholipid to about 30 µg protein per mg phospholipid. A preferred range is from about 0.2 to about 20 µg protein per mg phospholipid. In a preferred embodiment, the reagent comprises a mixture of phosphatidylserine and phosphatidylcholine in a ratio of from about 5:95 to about 95:5. A more preferred phosphatidylserine/phosphatidylcholine ratio is from about 15:85 to about 60:40. In a currently preferred embodiment, the phosphatidylserine/phosphatidylcholine ratio is from about 20:80 to about 30:70.

The reagent preferably contains calcium ions in an amount necessary for coagulation of the plasma sample. In a currently preferred embodiment, the concentration of calcium ions is from about 1 to about 20 mM. Calcium ions preferably are added as calcium chloride ($CaCl_2$), but other aqueous-soluble calcium salts may be used, for example, calcium gluconate.

In the present invention, the preferred buffer is Hepes buffer, but other buffers can be used, such as, for example, Tris or Imidazole buffers. The preferred concentration of buffer is the amount necessary for optimal coagulation of the plasma sample. The buffer concentration preferably is in the range of from about 25 mM to about 100 mM, most preferably, about 50 mM. The buffer preferably contains: NaCl (about 25 to 150 mM), glycine (about 0.1 to 10.0%), bovine serum albumin (about 0.1 to 1.0%), dextran (about 0.1 to 10.0%), polyethylene glycol (about 0.1 to 5%), calcium chloride (about 1 to 20 mM), antimicrobials such as sodium omadine (about 0.03 to 0.05%), ciprofloxacin (about 0.05 to 0.1 mg/mL) and/or propionic acid (about 20 to 200 mM) and a heparin antagonist to adjust the heparin sensitivity of the reagent, such as polybrene (about 1 to 50 µg/mL).

The preferred recombinant tissue factor for use in the present reagent formulation is recombinant rabbit tissue factor. Recombinant rabbit tissue factor can be prepared using well known cloning techniques. The cloning and sequencing of recombinant rabbit tissue factor was described by Andrews et al. in Gene, 98: 265–269 (1991). A cDNA library containing the DNA for obtaining the rabbit tissue factor gene is commercially available from Stratagene. The recombinant rabbit tissue factor currently most preferred for use in the reagents of the invention is a purified preparation of recombinant rabbit tissue factor which is enriched in the lipid binding domain, which is described hereinbelow.

The present invention further relates to a novel purified preparation of recombinant rabbit tissue factor. The recombinant rabbit tissue factor of the present invention has been engineered in such a way to facilitate purification by affinity techniques. Using this engineering design, the lipid binding sequence of the protein, which is important for biological activity, is intact in the purified protein. This design facilitates relipidation of the tissue factor protein into a liposome, or phospholipid vesicle, of a defined synthetic phospholipid blend.

The present purified preparation of recombinant rabbit tissue factor comprises an amino acid sequence defining from an N-terminus to a C-terminus: an extracellular domain, a lipid binding domain, an intracellular domain, and an affinity tag for selectively enriching the purified product for the lipid binding domain. The resulting purified preparation is enriched for, that is, has a significantly greater level of, recombinant tissue factor protein having the lipid binding domain compared to a recombinant tissue factor protein preparation lacking the affinity tag. The affinity tag is an amino acid sequence which has an affinity for a selected solid phase which is used in purifying the recombinant tissue factor protein. The affinity tag preferably is a plurality of consecutively linked amino acids, most preferably histidine. In a currently preferred embodiment, the affinity tag is a histidine hexamer $(His)_6$.

The present purified preparation of recombinant rabbit tissue factor protein has valuable characteristics which make it particularly well suited for use in the present PT reagents. For example, the preservation of the lipid binding region of the protein through the purification method renders the resulting purified preparation, which is enriched in the lipid binding domain, more amenable to relipidation when the protein is contacted with phospholipids. The present protein preparation can be used to produce a prothrombin time reagent having an ISI value of about 1.0, which is desirable. Reagents utilizing rabbit tissue factor protein are less sensitive to PIVKAs than reagents containing human or bovine tissue factors (Hemker, et al., Kinetic aspects of the interaction of blood clotting enzymes. III. Demonstration of an inhibitor of prothrombin conversion in vitamin K deficiency. *Thromb Diath Haemorrh*, (1968); 19: 346–63 and Denson KWE, Thromboplastin-sensitivity, precision and other characteristics. *Clin Lab Haematol*, (1988); 18: 315–28.

The present recombinant rabbit tissue factor protein preparation can be obtained from yeast cells which have been transformed with a transfer vector harboring the gene for rabbit tissue factor using art recognized techniques. As mentioned above, the sequence for rabbit tissue factors is known (Andrews et al., *Gene* (1991) 98:265–269). Yeast cloning systems are commercially available, for example, from Invitrogen. In the present invention, transformed yeast cells expressing the protein are disrupted and the protein is purified by the following method:

A histidine tail comprising a plurality of consecutively linked histidine residues is covalently linked to the C-terminus of the recombinant rabbit tissue factor protein. When the histidine-protein complex is applied to a metal-chelate column, the histidine portion of the binding protein will be bound by the column (Hochuli et al. *Biotechnology*, p. 1321, November 1988). The metal-chelate column comprises a resin derivatized with a chelating function (e.g., EDTA) and having a metal complexed with the chelating function. Preferred metals for this purpose include copper, zinc, cobalt and nickel. Nickel is currently most preferred for this purpose.

The histidine-tagged protein may be prepared according to the following currently preferred procedure in which six histidine residues are added to the C-terminus of the recombinant rabbit tissue factor protein. However, other His-proteins may be prepared; for example, any desired number of histidine residues may be added to the C-terminus of the recombinant rabbit tissue factor protein, provided the resultant His-tagged protein retains its biological activity and is retainable on a metal-chelate column. If desired, the His-protein can be further purified using other protein purification techniques known in the art.

A DNA fragment containing the rabbit tissue factor gene is isolated from a cDNA library by methods known in the art. The DNA fragment is then digested with restriction endonucleases to generate a restriction fragment containing rabbit tissue factor-encoding DNA. The tissue factor-encoding restriction fragment then is cloned into a polylinker site of a plasmid which allows for expression of the inserted DNA by placing the inserted DNA under control of a promoter useful in yeast expression vectors. The rabbit tissue factor-encoding plasmid then is transformed into an appropriate yeast host strain, and a recombinant clone containing His-rabbit tissue factor-encoding DNA is isolated.

The rabbit tissue factor-encoding clone is grown under conditions which do not allow for over-expression of the rabbit tissue factor gene until a desired optical density of the cell culture is reached. The culture is then induced to produce His-rabbit tissue factor protein, and the cells are grown until they are harvested. The cells are then centrifuged, and, if desired, the pellets can be frozen until ready for use. Rabbit tissue factor is purified from the cell pellet as follows. The cell pellet is thawed (if previously frozen) and resuspended in lysis buffer. The cells are disrupted and cell debris is eliminated by high speed centrifugation. The supernatant is applied to a pre-equilibrated metalchelate column, such as nickel, cobalt, copper or zinc, then clarified and neutralized to be ready for use.

Rabbit Tissue Factor (RTF) is a 260 amino acid residue glycoprotein. Specific detail on binding to and activation of FVII by RTF is not known, however, based on the known comparable specific activity and sequence homology between RTF and HTF, it is scientifically reasonable to expect that regions in RTF similar to those in HTF are equally important and perform equivalent functions:

Binding:
    Amino acids from 43 to 80
    Amino acids from 127 to 166
    Amino acids from 184 to 207 ($2^{nd}$ Cys loop)
    Amino acids from 218 to 239 (transmembrane or lipid binding region) (indispensable)

Amino acids 155 to 165, and 184 to 207 ($2^{nd}$ Cys loop) share both binding and activation functions, and are centrally located within the extracellular domain of the glycoprotein. Degradation of recombinant tissue factor may occur during in vitro expression of the protein due to proteolytic activity. These degraded byproducts would likely lack amino acid regions from either the N-terminal or C-terminal of the protein. Based on current knowledge of the structure/function relationship of tissue factor, the following analysis indicates the effect that missing regions of amino acids would have on the functional activity of tissue factor.

A. If degradation occurs from the N-terminal side of the protein the effect would most likely involve the binding regions, possibly reducing the binding affinity for FVII. The consequence of this degradation would be to attenuate the global tissue factor activity.

B. If degradation occurs from the C-terminal side of the protein, it would presumably not involve the binding properties, but some or the whole of the transmembrane region (amino acids 218 to 239) essential for the activation of FVII, making these degraded products still reactive to FVIIa, but unreactive to FVII. The global result would be a mixture with products equally competing for FVII molecules, and equally reactive to FVIIa, but with different reactivity to FVII. The consequences will be higher sensitivity to FVIIa than to FVII, depending on the ratio degraded to integral products.

Both of the above cases should behave differently in samples that, due to different circumstances, present a variation with time of the ratio FVII/FVIIa:

If tissue factor from case (B) were used to test those samples at different times, their results would be different.

If tissue factor from case (A) were used to test those samples at different times, their results would not be affected by the ratio variation.

To circumvent the problem described above, a sequence coding for a tail of six histidines ($(His)_6$) was attached to the 3' end of the recombinant RTF sequence (equivalent to the C-terminal in the protein). This design accomplishes the following:

(a) facilitates purification, by using metal affinity chromatography; and (b) maximizes the elimination of C-terminal-degraded products (case B), since these lack the $(His)_6$ tail, and will likely not be purified with the integral products.

The attachment of a $(His)_6$ tail on the 3' end of the rabbit tissue factor protein for purification minimizes the occurrence of this specific problem. Stated another way, the purification method used to obtain the present purified preparation of recombinant rabbit tissue factor protein preserves the presence of the lipid binding domain in the purified product resulting in a rabbit tissue factor protein that theoretically should be less sensitive to changes in the ratio of Factor VII:Factor VIIa.

Once the recombinant tissue factor protein is obtained, the PT reagent is formed by "relipidating" the protein to form a complex of the protein and associated phospholipids, which mimicks the natural TF-phospholipid complex. The phospholipids used in the method may be either natural or synthetic.

The invention further relates to a novel and unique relipidation method. In the purification protocol for the recombinant tissue factor protein, the recombinant protein is extracted into a surfactant solution (see Example 2). In prior art methods, the membrane protein is added to surfactant solubilized phosphoplipids which results in an isotropic solution of mixed phospholipid-protein-surfactant. Afterwards, the surfactant must be removed by methods such as dialysis, tangential filtration, dilution, or adsorption. (Moller, J.V. et al, *Prog. Protein-Lipid Interact.*, (1986), 2:147–196). In the state of the art, relipidation protocols for transmembrane proteins require complex procedures for surfactant removal. In the present relipidation procedure, the surfactant-solubilized recombinant protein is combined with the phospholipid blend, which is surfactant-free. Unexpectedly, we have found that removal of the surfactant after mixing the surfactant-solubilized tissue factor protein with phospholipids is not necessary to obtain a fully active and stable tissue factor preparation.

In the relipidation method of the invention, a solution containing the recombinant tissue factor is combined with a defined synthetic phospholipid blend. The synthetic phospholipid blend preferably comprises 1,2-dioleoyl-sn-glycerol-3-phosphocholine (phosphatidylcholine) and 1,2-dioleoyl-sn-glycero-3-[phospho-L-serine]

(phosphatidylserine), at a preferred molar ratio, to give the desired prothrombin time. The method comprises the steps of: (a) providing an aqueous solution, suspension or dispersion containing phospholipid vesicles or liposomes of the desired synthetic phospholipids; (b) admixing surfactant-solubilized tissue factor protein with said solution, suspension or dispersion; and (c) incubating the mixture produced in step (b) under conditions and for a time sufficient to permit said protein to associate with said phospholipid vesicles. The method further may comprise the additional steps of admixing the solution obtained after step (c) with a buffer containing calcium ions. The resulting formulation may be a single vial reagent, which can be either liquid or lyophilized. This formulation strategy improves lot-to-lot consistency of the reagent. Sensitivity to heparin, or other anticoagulants, may be adjusted by the addition of a heparin antagonist, such as polybrene.

The reagents of the present invention have many applications, including measuring prothrombin time, determining fibrinogen levels, monitoring patients in oral anticoagulant therapy, and determining factor levels. The reagent activates the extrinsic pathway of coagulation which detects activity of Factors II, V, VII and X. Overall percent activity of a Factor or Factors can suggest clinical manifestations within this pathway. The reagent also can be used for clinical monitoring of patients on oral anticoagulant therapy, e.g., coumadin (also known as warfarin). Coumadin is a vitamin K antagonist which, when administered, can interfere with the ability of the liver to carboxylate the glutamyl residues of the vitamin-K dependent Factors II, VII, IX, X, Protein C and Protein S. The noncarboxylated forms of Factors II, VII, IX and X lack the correct post-translational modifications and thus are less functional, resulting in prolongation of clot formation. These protein products are typically referred to as PIVKA's (protein induced by vitamin K absence or antagonist). See, Hemker and Jie, Ch. 5, "Proteins induced by vitamin K absence (PIVKAs):effect of coumarins on circulating clotting factors", *Oral Anticoagulants*, L. Poller and J. Hirsh (Eds.), Arnold (1996).

The present rabbit recombinant tissue factor can also be used to develop any modification of the prothrombin time (PT). Examples of such modified PT tests for which the reagents of the invention can be used include the following:
1) Prothrombin Consumption Test A generalized screening test for the detection of deficiencies in Factors V, VII, IX or XI or XII, described by Palkuti HS. In "Laboratory monitoring of anticoagulant therapy." *J. Med. Tech.*, (1985), 2:81–86; and Owen CA Jr., Thompson JH Jr. in "Soybean phosphatides in prothrombin-consumption and thromboplastin-generation tests: their use in recognizing thrombasthenic hemophilia". *Am. J. Clin. Pathol.*, (1960); 33:197–208. Biggs R, Douglas AS. "The thromboplastin generation test" *J. Clin. Pathol.*, (1953), 6:23–29.
2) Prothrombin Proconvertin Test A screening test that reflects the effect of oral anticoagulant therapy on Factors II, VII, IX and X, described by Owren PA, Aas K. in "The control of dicumarol therapy and the quantitative determination of prothrombin and proconvertin" *Scand. J. Clin. Lab. Invest.*, 3:201–208; and Ware AG, Stragnell R. "An improved on-stage prothrombin method" *Am. J. Clin. Pathol.*, (1952), 22:791–797.
3) Tissue Thromboplastin Inhibition Test A screening test that detects Lupus like inhibitors by enhancing the ability of these inhibitors to interfere with assembly of the prothrombinase complex. Ref: Brandt JT, Triplett DA. "The effect of phospholipid on the detection of lupus anticoagulant by the dilute Russell viper venom time" *Arch. Pathol. Lab. Med.*, 1989; 113:1376–1378.

The present recombinant rabbit tissue factor based PT reagents have less sensitivity to PIVKAs, and therefore are useful for monitoring patients on oral anticoagulation therapy and those with liver impairment (Denson, K.W.E. et al. "The Characterisation of Recombinant Rabbit Tissue Factor (rRTF) and the PIVKA Inhibitor" Submitted for publication). Currently available reagents based on human thromboplastin may not be suitable for use with these patients due to their sensitivity to PIVKAs. A difference between previous reagents and the reagents of the present invention may be reflected in the INR (international normalized ratios) values, in which reagents based on human thromboplastins show deviations in warfarin controls and liver patients (Kovacs, M. J. et al., "Assessment of the Validity of the INR System for Patients with Liver Impairment" *Thromb. Haemost.* 71:727–730 (1994)). An advantage of the present rabbit based recombinant PT reagent is reduction of such deviations in INR, which allows the application of this reagent both in monitoring oral anticoagulant therapy and liver impairment in patients. Therefore, the INR system could be used on plasma from patients undergoing oral anticoagulant therapy or having any type of liver impairment without any interference from PIVKAs in the patient plasma.

PT time and fibrinogen levels can be determined using the reagents of the present invention with currently available clinical coagulation analyzers (such as the ACL® or ACL Futura® available from Instrumentation Laboratory, Lexington, Mass.), in accordance with typical protocols.

In a typical protocol, 100 $\mu$l of the PT reagent and 50 $\mu$l of plasma are warmed to a temperature of 37° C. The reagent and the plasma samples then are mixed, which triggers the coagulation reaction. Formation of the clot is detected by a detector, e.g., by a change in optical density, or by a change in viscosity of the sample. The amount of time required for a clot to form is the prothrombin time. This process typically is fully automated, but may be performed manually. In the automated process, the clinician merely loads the reagent and the plasma sample into the automated coagulation analyzer, which carries out the heating, mixing and detecting steps. In these protocols, fibrinogen levels can be determined by the following steps. Thrombin (Factor IIa) generated at the endpoint of the extrinsic cascade converts fibrinogen to fibrin in the patient's plasma sample. The fibrin molecules self-aggregate to form a clot. The change in absorbance or light scatter is directly proportional to the amount of fibrinogen present in the sample, and can be determined using an appropriate algorithm (see FIG. 1).

The reagents of the invention can be used in place of currently used PT reagents in most clinical instruments for automated and semi-automated PT assays, as well as manual methods. The majority of prothrombin time reagents that are currently available in the market are based on crude rabbit tissue factor, and have more lot-to-lot variability than the present reagents. Using the present reagents, the desired sensitivity for oral anticoagulant therapy (ISI≈1.0) can be achieved while maintaining factor sensitivity, similar to the crude rabbit based reagents currently used. The following examples are intended to illustrate specific embodiments aspects of the present invention, and are not intended to be limiting in any way.

EXAMPLES

Example 1

Recombinant PT Reagent Formulation—General Protocol.

The following protocol describes the preparation of a PT reagent in which recombinant rabbit tissue factor is relipidated into a defined liposome composition at an optimum tissue factor-to-liposome ratio. After relipidation, the protein-phospholipid complex is added to a formulation buffer containing calcium, polybrene (heparin antagonist), and stabilizers. The formulation is adjusted to reach a PT time of about 10–13 seconds for the normal control by addition of the relipidated protein.

Preparation of Liposome Suspension and Tissue Factor Relipidation

A synthetic phospholipid blend from 0.5 to 10 mM of defined composition (phosphatidylserine/phosphatidylcholine, 15:85 to 30:70 M/M) is filtered through a hydrophilic polyvinylidene fluoride filter. The stock protein preparation containing recombinant rabbit tissue factor in buffer containing 0.1% non-ionic surfactant, prepared as described in Example 2, is diluted from 1:10 to 1:1500 into the filtrate. The ratio of protein to phospholipids can be optimized to achieve the desired prothrombin time. The tissue factor protein is incubated with the liposome suspension at 37° C. for a minimum of 30 minutes to ensure association of the protein with the liposome vesicles. After the incubation step, the protein/phospholipid, is formulated in such a way to achieve the desired reagent properties. The protein/phospholipid is added to a formulation buffer, as described below, in a dilution range from 10 to 80 fold.

Preparation of a Liquid Formulation

A formulation buffer is prepared, preferably Hepes from 50 to 100 mM, which contains NaCl (150 mM), glycine (1%), bovine serum albumin (0.3%), polyethylene glycol (2%), calcium chloride (10 mM), antimicrobials such as sodium omadine (0.05%), ciprofloxacin (0.05 mg/mL), and/or propionic acid (20 mM) and a heparin antagonist such as polybrene (5 $\mu$g/mL) to adjust the heparin sensitivity of the reagent. To this formulation buffer, which is filtered through a 0.2$\mu$ filter, the protein-phospholipid mixture is added. The liquid formulation is then incubated at 37° C. for a specified time. To reach the desired prothrombin time, i.e., a normal PT time of 10–13 seconds, the amount of protein-phospholipid mixture may be increased if necessary. The formulation can be optimized to reach the desired sensitivity to factors, and ISI (ISI≈1.0) by adjusting the excipients in the formulation.

Table I shows the lot-to-lot reproducibility of three lots of liquid reagent formulation prepared according to the above-described method using the preferred ranges. The PT is obtained by adding 100 $\mu$L of reagent (recombinant rabbit PT reagent) to 50 $\mu$L of patient plasma and initiating the activation of the extrinsic pathway, which results ultimately in the conversion of fibrinogen to fibrin with formation of a solid gel. PT times were determined using an ACL® 300 clinical coagulation analyzer (Instrumentation Laboratory, Lexington, Mass.) in acordance with the manufacturer's recommended protocols. The results obtained demonstrate the consistency of reagent lots with respect to ISI and prothrombin time determinations which are an important clinical consideration.

TABLE I

Lot to Lot Reproducibility - Liquid Reagent

| Reagent Lot No. | ISI | Normal Mean (Prothrombin Time) | Normal Control Plasma | Abnormal Control Plasma |
|---|---|---|---|---|
| 1 | 1.00 | 12.5 | 11.8 | 22.9 |
| 2 | 0.9801 | 12.65 | 12.4 | 23.7 |
| 3 | 1.0047 | 12.62 | 11.8 | 22.4 |

Preparation of a Lyophilized Formulation

A formulation buffer is prepared, preferably Hepes from 50 to 100 mM, which may contain NaCl (50 mM), glycine (5%), bovine serum albumin (0.3%), dextran (5%), calcium chloride (10 mM), antimicrobials such as sodium omadine (0.05%), ciprofloxacin (0.05 mg/mL) and a heparin antagonist to adjust the heparin sensitivity of the reagent, such as polybrene (5 $\mu$g/mL). To this formulation buffer, which is filtered though a 0.2$\mu$ filter, the protein-phospholipid mixture is added. The formulation is then incubated at 37° C. for a specified time and subsequently lyophilized. To reach the desired prothrombin time, i.e. a normal PT time of 10 to 13 seconds, the amount of protein-phospholipid mixture may be increased if necessary. The formulation can be optimized to reach the desired sensitivity to factors, and ISI (ISI≈1.0) by adjusting the excipients in the formulation.

Table II shows the lot-to-lot reproducibility of three lots of lyophilized reagent formulation made according to this method from using the preferred ranges. The lyophilized reagent was reconstituted in water and the PT (prothrombin time) determined. The PT is obtained by adding 100 $\mu$L of reagent (recombinant rabbit PT reagent) to 50 $\mu$L of patient plasma and initiating the activation of the extrinsic pathway, which results ultimately in the conversion of fibrinogen to fibrin with formation of a solid gel. The prothrombin time was determined using the ACL® 300 instrument as described above. These results demonstrate the consistency of these lots with respect to ISI and normal mean determination which is an important clinical consideration.

TABLE II

Lot to Lot Reproducibility - Lyophilized Reagent

| Reagent Lot No. | ISI | Normal Mean (Prothrombin Time) | Normal Control Plasma | Abnormal Control Plasma |
|---|---|---|---|---|
| 1 | 1.0396 | 11.17 | 10.6 | 22.4 |
| 2 | 1.0497 | 11.20 | 11.2 | 23.8 |
| 3 | 1.0722 | 11.34 | 10.7 | 22.3 |

The recombinant rabbit PT reagent also can be used to determine fibrinogen levels which provides additional diagnostic value to the PT results. Table III shows an example of a PT and fibrinogen calibration curve results using an automated clinical coagulation analyzer (ACL® Futura®). The PT and fibrinogen values are obtained by adding 100 $\mu$L of reagent (recombinant rabbit PT reagent) to 50 $\mu$L of plasma and initiating the activation of the extrinsic pathway as described above. A calibrator plasma with an assigned fibrinogen value is diluted to generate the calibration curve. The PT and fibrinogen concentration of the plasma sample can be simultaneously determined by a thrombokinetic measurement by relating the absorbance or light scatter during clotting. FIG. 1 shows the fibrinogen values (mg/dL) from plasma samples determined using the recombinant rabbit PT reagent as compared to a conventional rabbit thromboplastin (correlation=0.998). The conventional thromboplastin was IL Test™ PT-fib H5 Plus (P/N 84698-10) (available from Instrumentation Laboratory, Lexington, Mass.).

TABLE III

PT and PT- based fibrinogen calibration curve using recombinant rabbit PT reagent with an automated clinical coagulation analyzer

| % Calibration Plasma | PT Seconds | Fibrinogen (mg/dL) | Delta Absorbance |
|---|---|---|---|
| 100 | 11.7 | 262.0 | 816.7 |
| 50 | 19.6 | 131.0 | 433.7 |
| 25 | 38.8 | 65.5 | 195.0 |
| correlation coefficient (r) | 0.998 | 0.996 | |

Example 2
Production of Recombinant Rabbit Tissue Factor from Yeast

Recombinant Rabbit Tissue Factor (rRTF) is produced in recombinant *Pichia pastoris* cells obtained according to the following general protocol:

A fragment of DNA harboring the complete RTF-gene was isolated from a commercial Rabbit Heart cDNA library in λZapII purchased from Stratagene (Cat. #936902).

A sequence coding for $(His)_6$ tail was added to the 3' end of the translated sequence of the RTF gene, and engineered to be compatible with the Pichia pastoris transfer vector pHIL-S1 (obtained from Invitrogen), and inserted into it to be in phase with the PHO1 signal sequence, and under the direction of the AOX1 promoter.

Other sequences of interest included in this plasmid are:
The HIS4 open reading frame as a rescue marker
The Ampicillin resistance gene
Flanking regions of the 5' and 3' ends of the AOX1 gene, to facilitate recombination Wild type *Pichia pastoris* GS115 cells (obtained from Invitrogen), were transformed with the above-mentioned recombinant P pastoris transfer vector carrying the RTF gene. After recombination, one of the isolated RTF-producing clones was selected, based on its higher expression of active RTF, and its production improved by optimizing fermentation conditions.

The recombinant yeast cells containing rRTF were disrupted and protein extracted in buffer containing non-ionic surfactant. The preferred buffer is 50 mM PIPES, 500 mM NaCl, 0.76% Emulphogen, pH 7.8, but other buffers and non-ionic surfactants, such as Triton X-100 or NP-40, may be substituted.

The resulting crude homogenate was clarified and prepared for chromatography by adjusting the solution to pH to 7, diluting the pH adjusted mixture with buffer, followed by high speed centrifugation. The rRTF was isolated from the clarified homogenate by metal chelate affinity chromatography.

Following elution from the column, rRTF was further enriched by a precipitation at pH 4, at 24° C. and clarified by high speed centrifugation. Finally, the protein solution was adjusted to neutral pH. The final solution containing rRTF was composed of 100 to 500 μg protein in the preferred buffer of 50 mM Tris-Acetate, 500 mM NaCl, 0.1% Emulphogen, pH 7.1. Other buffer compositions containing other non-ionic surfactants, such as mentioned above, may be used. The product was frozen at −70° C. for storage until use. Except for the 24° C. incubation, all steps of manufacture were performed at 4° C.

EQUIVALENTS

Those skilled in the art may be able to ascertain many equivalents to the specific disclosure described herein. Such equivalents are intended to be included within the scope of the following claims.

What is claimed is:

1. A method of preparing a liquid or a lyophilized reagent for determining prothrombin time or fibrinogen levels in a plasma sample, the method comprising the steps of:
   (a) providing a solution, suspension or dispersion containing a phospholipid vesicle; wherein said solution, suspension or dispersion is surfactant free;
   (b) admixing surfactant solubilized tissue factor protein with said solution, suspension or dispersion; and
   (c) incubating the mixture produced in step (b) under conditions and for a time sufficient to permit said surfactant-solubilized tissue factor protein to associate with said phospholipid vesicle to produce a reagent capable of inducing coagulation in the plasma sample without removal of the surfactant.

2. The method of claim 1, wherein the isolated tissue factor protein of step (b) is a recombinant rabbit tissue factor protein.

3. The method of claim 1 comprising the additional step of admixing the solution containing the protein-containing phospholipid vesicle of step (c) with a formulation buffer.

4. The method of claim 3, wherein the isolated tissue factor protein of step (b) is a recombinan rabbit tissue factor protein.

5. A purified preparation of recombinant rabbit tissue factor, said preparation comprising:
   recombinant rabbit tissue factor comprising
      an amino acid sequence defining from an N-terminus to a C-terminus,
         (a) an extracellular domain,
         (b) a lipid binding domain,
         (c) an intracellular domain, and
         (d) an affinity tag for use in selectively enriching said recombinant rabbit tissue factor;
      wherein the purified preparation is enriched for the recombinant rabbit tissue factor protein having the lipid binding domain relative to a recombinant rabbit tissue factor without the affinity tag.

6. The purified preparation of claim 5, wherein the affinity tag comprises a plurality of consecutively linked histidine amino acids.

7. The purified preparation of claim 6, wherein the affinity tag comprises a $(His)_6$ sequence.

8. The purified preparation of claim 5, wherein the recombinant rabbit tissue factor reacts with Factor VII and Factor VIIa.

9. The purified preparation of claim 5, wherein the recombinant rabbit tissue factor can be used to produce a prothrombin time reagent having an ISI value of about 1.0.

10. The purified preparation of claim 5, wherein the recombinant rabbit tissue factor is less sensitive to PIVKAs in a plasma sample relative to human or bovine tissue factor.

11. A liquid or lyophilized reagent for determining prothrombin time or fibrinogen levels in a plasma sample, the reagent consisting essentially of:
   (a) a surfactant-solubilized recombinant rabbit tissue factor protein;
   (b) a phospholipid selected from the group consisting of phosphatidylcholine, phosphatidylserine, and a combination thereof; and
   (c) a buffer system;

wherein the phospholipid contains a mixture of phosphatidylserine and phosphatidylcholine in a ratio from about 20:80 to abut 30:70.

12. The reagent of claim 11, wherein the protein to lipid ratio is from about 0.05 µg protein/mg phospholipid to about 30 µg protein/mg phospholipid.

13. The reagent of claim 12, wherein the protein to lipid ratio is from about 0.2 µg protein/mg phospholipid to about 20 µg protein/mg of phospholipid.

14. The reagent of claim 11, wherein the buffer system contains calcium ions in an amount sufficient for coagulation of the plasma sample.

15. The reagent of claim 11 or 14, wherein the buffer system has ionic strength sufficient to support coagulation in the plasma sample.

16. The reagent of claim 11 or 14, wherein the buffer system contains Hepes.

17. The reagent of claim 15, wherein the buffer system contains Hepes.

18. The reagent of claim 11, wherein the tissue factor protein comprises a purified preparation of recombinant rabbit tissue factor comprising:

an amino acid sequence defining from an N-terminus to a C-terminus,
(a) an extracellular domain,
(b) a lipid binding domain,
(c) an intracellular domain, and
(d) an affinity tag for use in selectively enriching said recombinant rabbit tissue factor, wherein the purified preparation is enriched for the recombinant rabbit tissue factor protein having the lipid binding domain relative to a recombinant rabbit tissue factor without the affinity tag.

19. A method for measuring the amount of fibrinogen in a plasma sample, the method comprising the steps of:
(a) providing the plasma sample;
(b) providing the reagent of claim 11 or 18;
(c) mixing the reagent of step (b) with the plasma sample of step (a); and
(d) determining clot formation.

* * * * *